US008380166B2

(12) United States Patent
Diebold et al.

(10) Patent No.: US 8,380,166 B2
(45) Date of Patent: Feb. 19, 2013

(54) APPARATUS FOR AND METHOD OF OPERATING A MOBILE COMMUNICATION DEVICE SENSOR

(75) Inventors: Michael Diebold, Berlin (DE); Jens Potschadtke, Erlangen, DE (US); Günter Behrens, Berlin (DE); Sven Bode, Berlin (DE)

(73) Assignee: Biotronik CRM Patent AG (CH)

( * ) Notice: Subject to any disclaimer, the term of this patent is extended or adjusted under 35 U.S.C. 154(b) by 1097 days.

(21) Appl. No.: 11/219,301

(22) Filed: Sep. 2, 2005

(65) Prior Publication Data

US 2006/0052084 A1 Mar. 9, 2006

(30) Foreign Application Priority Data

Sep. 3, 2004 (DE) .......................... 10 2004 043 211

(51) Int. Cl.
*H04M 1/66* (2006.01)
*H04W 4/00* (2009.01)
*H04M 1/00* (2006.01)

(52) U.S. Cl. .................. 455/411; 455/432.1; 455/435.1; 455/553.1

(58) Field of Classification Search .................. 455/411, 455/432.1, 552.1
See application file for complete search history.

(56) References Cited

U.S. PATENT DOCUMENTS

| 4,972,355 | A | * | 11/1990 | Mullins ....................... 455/435.1 |
| 5,301,357 | A |   | 4/1994  | Thompson |
| 5,594,945 | A | * | 1/1997  | Lewis et al. .................. 340/7.27 |
| 5,742,509 | A | * | 4/1998  | Goldberg et al. ............. 701/211 |
| 5,742,904 | A | * | 4/1998  | Pinder et al. ............... 455/404.1 |
| 5,752,976 | A |   | 5/1998  | Duffin et al. |
| 6,026,293 | A | * | 2/2000  | Osborn ......................... 455/411 |
| 6,434,429 | B1 | * | 8/2002 | Kraus et al. .................... 607/60 |
| 6,490,487 | B1 | * | 12/2002 | Kraus et al. .................... 607/60 |
| 6,516,188 | B1 |   | 2/2003 | New et al. |
| 6,553,262 | B1 |   | 4/2003 | Lang et al. |
| 6,563,809 | B1 |   | 5/2003 | Proctor, Jr. et al. |
| 6,611,197 | B1 |   | 8/2003 | Ayerst et al. |
| 6,741,852 | B1 | * | 5/2004 | Mohrs ........................... 455/411 |
| 2001/0029321 | A1 | * | 10/2001 | Beetz et al. ................... 600/300 |

FOREIGN PATENT DOCUMENTS

| WO | 0041486 | 7/2000 |
| WO | 0203719 | 1/2002 |
| WO | WO 02/03719 | 1/2002 |
| WO | 03095024 | 11/2003 |
| WO | 2004066656 | 8/2004 |

OTHER PUBLICATIONS

Revision of the Commission's Rules to Ensure Compatibility with Enhanced 911 Emergency Calling Systems, May 13, 1999, http://www.fcc.gov/Bureaus/Wireless/Orders/1999/fcc99096.txt.

* cited by examiner

*Primary Examiner* — Huy C Ho
(74) *Attorney, Agent, or Firm* — Hahn Loeser & Parks LLP; John J. Cunniff

(57) ABSTRACT

A wireless apparatus includes a cellular radio interface that is adapted to perform a data exchange by way of a wireless data network, a user identity module containing information for authorization of a user for use of wireless networks, and a control unit which controls establishment and implementation of the data exchange. A second control unit is included and adapted to limit, in respect of the duration of its effect, a rejection of the user identity module expressed by the locally available wireless data networks in logging on to the wireless data network by suitable control of the first control unit in the further course of the log-on process by bypassing communicated information about the rejection.

16 Claims, 7 Drawing Sheets

APPARATUS FOR AND METHOD OF OPERATING A MOBILE COMMUNICATION DEVICE SENSOR

This U.S. utility patent application claims priority to German patent application serial no. 10 2004 043 211.2 filed Sep. 3, 2004.

TECHNICAL FIELD

The embodiments of the present invention pertains to a wireless data interface (telemetry data interface), and more specifically, to a cellular radio interface that is adapted to perform a data exchange by way of a wireless data network, and which further controls establishment and implementation of the data exchange on the basis of items of information stored on a user identity module.

BACKGROUND OF THE INVENTION

Wireless data devices are known in principle and are used in medical monitoring for high-risk patients or remote maintenance and diagnosis of technical equipment. Such equipment may, communicate technical or medical data to a data acquisition and evaluation center by way of a cellular radio or wireless data network, and may possibly receive instructions from the same.

In that respect, portable devices are often utilized for the home monitoring of high-risk patients, such devices having a second telemetry interface for communication with an electromedical implant. Modern electromedical implants, in particular cardiac pacemakers, defibrillators and the like afford physician and patients a very high degree of security and comfort by virtue of those home-monitoring functions.

In that respect the implant processes diagnosis and therapy information and transmits items of information to an external patient device by way of a telemetry interface. From there the data are passed to what is referred to as a home monitoring service center (HMSC) where they are stored and displayed for the physician. In that way the physician can be informed directly about therapy progress and the current state of health of his patients and enjoys the possibility of reacting quickly to possible changes in health.

Without home monitoring the physician can obtain those items of information only in the context of an examination of the patient. In critical situations, that would result in unwanted delays in the flow of information. In addition any examination involves a considerable amount of time, both for the physician and the patient. Frequent examination has an adverse effect on the mobility and quality of life of the patient.

In home monitoring, the implant information is sent via the patient device (see U.S. Pat. Nos. 6,553,262 and 5,752,976) in the background without the patient being limited in terms of leading a normal life. In other words, the patient enjoys the security of physician monitoring without the stress of frequent examinations.

In the case of the technical device, continuous monitoring means that it is possible to recognize particular operating conditions so that further operation of the device can be guaranteed.

As the freedom of movement of a patient is not to be unnecessarily restricted, data transmission is preferably effected by way of one of the extensively available cellular radio networks, in particular the GSM, UMTS or a CDMA network. Data transmission by way of a WLAN network can also be envisaged. The advantage of ease of connection by way of one of those wireless communication networks is rather in the foreground, but it is also possible to imagine movable items of equipment in respect of which the aspect of unrestricted mobility is also to be considered. Thus a similar device could be used in vehicles involved in goods delivery or personal transport in order, for example, to communicate to a control center various data including location, loading and technical data such as the tank filling level or the temperature of the load space. In that case the vehicle and the device are usually combined to form one unit.

The development of a device of the described kind together with the cellular radio interface may be very complicated and expensive. In practice, therefore it may be made up in part from prefabricated modules, which afford given functions. That applies in particular to the cellular radio interface, which is normally embodied by a cellular telephone incorporated into the device or a prefabricated cellular radio module with full functional extent.

In order to authenticate the access authorization to a wireless communication network devices equipped with a cellular radio interface are provided with a user identity module which uniquely identifies the device or its operator on the basis of items of information stored on the user identity module. When logging on to a wireless communication network the device communicates those items of information to that network which then checks the access authorization of the device by a comparison with a centrally stored copy. Identification is inter alia therefore a necessary prerequisite for use of a mobile service as it is only thereby that the connection costs incurred can be billed. Therefore it is also always involved in so-called 'roaming', that is to say the use of network resources and services of cellular radio network operators in other region or countries. In the case of a device which is designed to communicate by way of a GSM network the user identity module is in the form of what is referred to as a SIM card, the copy of the access authorization is stored in what is referred to as the 'home location register' (HLR).

If an access authorization to the wireless communication network in question cannot be established, the wireless communication network communicates to the device, which is seeking to log on a request to refrain from further log-on attempts in relation to the same network in order to husband the resources thereof. As a standard procedure, cellular telephones and cellular radio modules take account of that information about a rejection and refrain from further log-on attempts in relation to the communication network in question. A further log-on attempt can be triggered only by operating the keypad of the cellular telephone or the cellular radio module. If there is no keypad or if it is inaccessible a further log-on procedure cannot be initiated at all.

A log-on attempt in relation to a communication network is also rejected thereby when checking of the access authorization is not possible. That occurs, for example, when a connection could not be made to the HLR, due to a fault. Such accesses can be the subject of interference particularly when roaming because of the more complicated access to the HLR.

Under some circumstances, a device may be rejected by all receivable networks and of its own accord ceases all further attempts to form a connection by way of a wireless communication network. It can then only be moved to make further log-on attempts by virtue of external intervention. As however either the user of the device is not to be bothered due to a complicated user interface or however there is no one at all present on the spot, operation of a device of the described kind in accordance with the state of the art can no longer be guaranteed.

Therefore, it would be advantageous to provide a device and a method of operating such a device, which even after rejection by all receivable wireless communication networks, permits a communication of the device with the home monitoring service center if the cause of the rejection is no longer there.

SUMMARY OF THE INVENTION

According to one aspect of an embodiment of the subject invention, a second control unit is adapted to render inoperative, or to limit in respect of the duration of its effect, a rejection of the user identity module expressed by the locally available cellular radio or wireless data networks in logging on to the cellular radio or wireless data network by suitable control of the first control unit in the further course of the log-on process by bypassing or erasing communicated information about the rejection.

Another aspect of an embodiment of the subject invention is attained by a method which renders inoperative, or limits in respect of the duration of its effect, a rejection of the user identity module expressed by the locally available cellular radio or wireless data networks when logging on to the cellular radio or wireless data network by bypassing or erasing communicated messages about the rejection.

In yet another aspect of an embodiment of the subject invention, the device it is portable.

Still another aspect of an embodiment of the subject invention includes a device that has a second telemetry data interface by way of which it can communicate with an electromedical implant, for example a cardiac pacemaker, and permits home monitoring of a patient by evaluation and/or forwarding of the technical and medical data received from the electromedical implant, by way of the first telemetry data interface to an HMSC.

In another embodiment, the communication connection is effected by way of the cellular radio interface and/or by way of a GSM, a UMTS, a CDMA or a WLAN network. In that case, the device can have any choice of interfaces with networks of the specified kinds. This may facilitate adaptation of the device to the actual conditions of the respective market and enhances the probability of a network connection in the corresponding environment.

At least one of the control units of the device may be adapted to recognize unsuccessful log-on because of rejection by all cellular radio or wireless data networks available on the spot. Thereupon, the particular steps of the method of an embodiment of the subject invention can be initiated.

In a further embodiment, the configuration of the first control unit may be adapted to produce a list of the locally receivable cellular radio or wireless data networks and make it available to the second control unit. In a particular variant of this embodiment, the second control unit may be adapted, after a failed log-on, to select another network from the list and to cause the first control unit to make a log-on attempt in relation to that network even if that network had already rejected a log-on in a preceding attempt. The second control unit may be adapted to cause a fresh list to be produced by the first control unit after unsuccessful log-on attempts in relation to all networks of the list.

In yet another embodiment, the second control unit may include a timer or may be connected to a timer. The control unit is designed in such a way that, after a failed log-on, it allows the elapse of a predetermined period of time measured by the timer, before it initiates a further log-on attempt in relation to the same network. That husbands both the resources of the network operators and also the battery life of the device.

In still another embodiment, the control units may be adapted to output and/or execute AT commands. AT commands represent a generally accepted standard, for which reason many prefabricated components and modules operate therewith; the use thereof therefore simplifies the structure of the overall system.

In even another embodiment, the second control unit may include a timer or is connected to a timer. It is so designed that it defers repeated log-on attempts that are unsuccessful in relation to all available cellular radio or wireless data networks for a given time, which is measured by the timer. Once again that measure husbands both the resources of the network operators and also those of the device.

The second control unit may advantageously be designed to predetermine and alter operating parameters such as, for example, the pause between two log-on attempts, the maximum number of log-on attempts and the maximum time which is used for a log-on attempt before it is broken off as being unsuccessful. The operating parameters to be adapted can be determined automatically in accordance with an algorithm as in a pseudo-random process or another process. In a particular variant of this embodiment, the second control unit is directly or indirectly connected to the cellular radio interface and so designed that the choice of the parameters can be affected and triggered from the HMSC by way of the cellular radio interface. In that way, in operation, it is still possible to effect optimizations in respect of the operating parameters, which for example allow a longer battery life or adapt the device to particular prevailing conditions of a country where it is located. A method involves firstly detecting an unsuccessful log-on by virtue of rejection by all cellular radio or wireless data networks available on the spot.

In another embodiment of the methods referred to, a list of the locally receivable cellular radio or wireless data networks is produced and a sequence of the individual entries in the list is established. In a particularly variant of that method, the sequence of the list of the locally receivable cellular radio or wireless data networks is determined in accordance with the respective reception strength so that networks of a higher reception strength are preferred. That measure increases the probability of error-free data transmission if firstly a log-on attempt is affected in relation to a better receivable network and the log-on is successful.

In another embodiment of the method, after a failed log-on in relation to a network, the network in the list which is next in the sequence thereof is selected and a log-on attempt is implemented in relation to that network, even if that network had already rejected a log-on in a preceding attempt.

After unsuccessful log-ons, in relation to all networks in the list, a new list is produced. That takes account of changes in the availability of networks, which are caused for example by a change in location while the method is being carried out.

In another embodiment of the method, after a predetermined time, a log-on attempt in relation to a network is considered to be failed and it is broken off if no positive return message has been given by the network.

In still another embodiment of the method, after a failed log-on, a predetermined time is allowed to elapse before a further log-on attempt is initiated in relation to the same network. The advantage of that measure lies in husbanding of resources on both sides.

In a further variant of the method, after a predetermined number of failed log-ons, further log-on attempts in relation to the same or other networks are deferred for a predetermined time. In this case also the respective resources are husbanded both on the part of the network operators and the device.

The variants of the method involve establishing whether a log-on attempt in relation to one of the available networks was successful and, in the event of success, the method is then concluded.

BRIEF DESCRIPTION OF THE DRAWINGS

The invention will now be described in greater detail by means of embodiments by way of example with reference to the Figures in which.

DETAILED DESCRIPTION OF THE INVENTION

Figure 1:
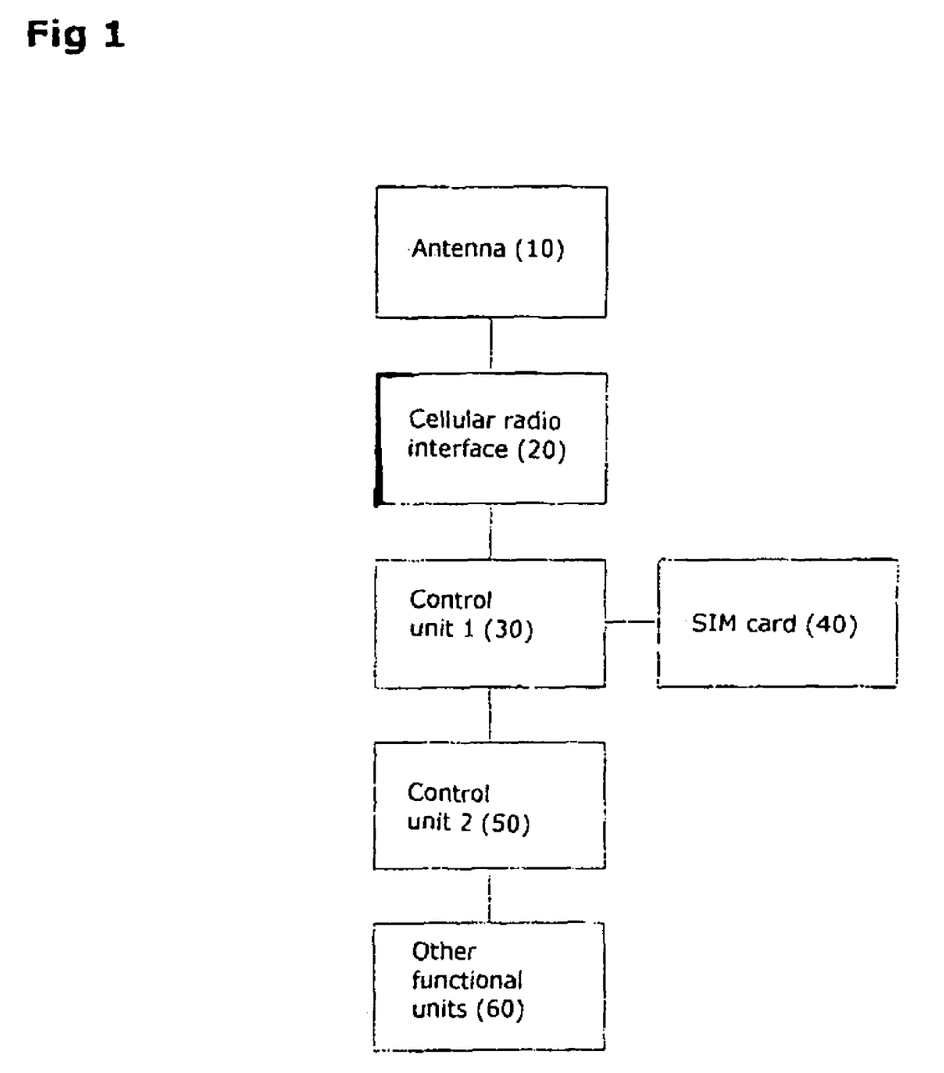
FIG. 1 shows a block diagram of a device of the kind claimed in claim 1.

FIG. 1 shows by way of example a block diagram of an embodiment of the subject invention in its general form. Essential component parts of the device are set out in the block diagram. An antenna 10 is connected to a cellular radio interface 20, which may be controlled by a first control unit 30. The control unit is connected to a SIM card 40, which besides other items of information for operation of the cellular radio interface also includes those items of information for identification of the user and for proving the authorization of the user to use the cellular radio service. In accordance with the current embodiment of the invention there is provided a second control unit 50 connected to the control unit 30. In the embodiment shown in FIG. 1 other functional units 60, which perform further functions of the device are connected to the second control unit 50 directly and to the first control unit 30 indirectly. It is also possible to envisage other configurations in which the other functional units 60 are connected directly to the first control unit 30 and/or indirectly to the second control unit 50.

Figure 2:
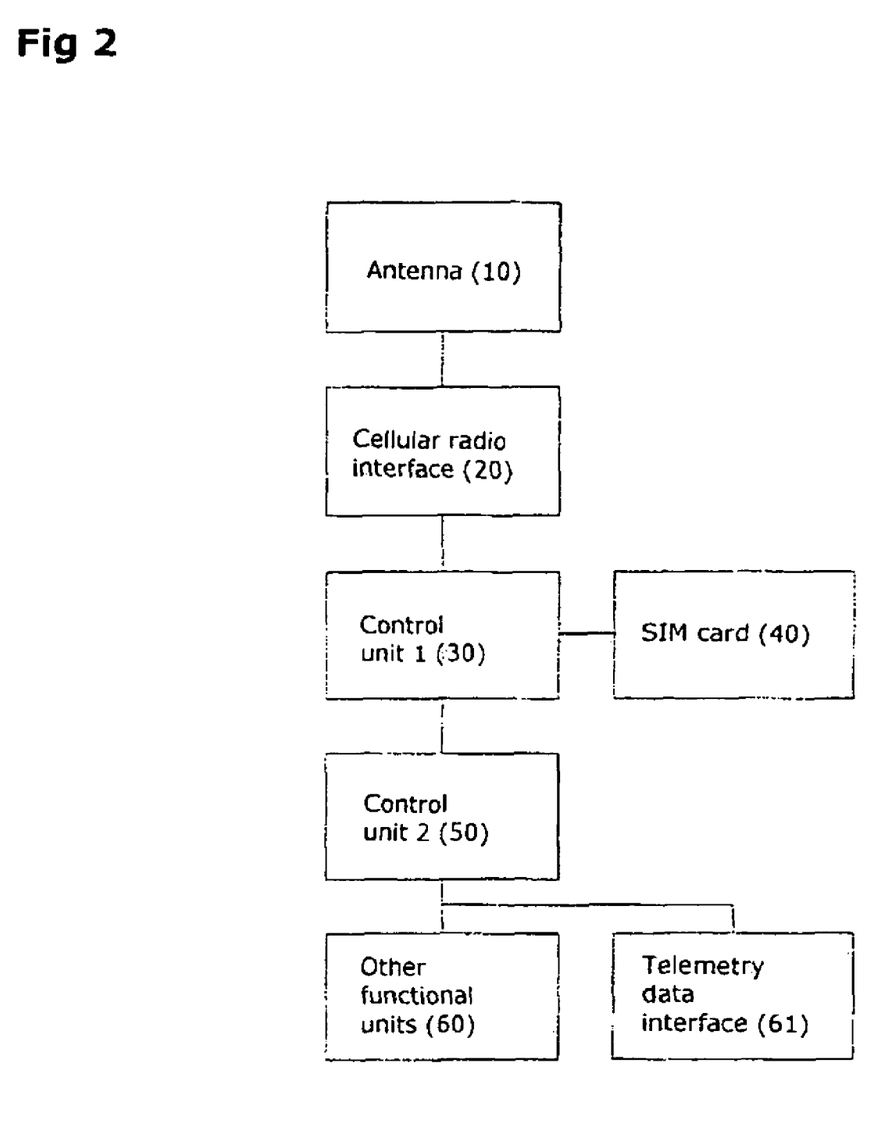
FIG. 2 shows a block diagram of a device of the kind claimed in claim 1, which is equipped with a second telemetry data interface.

FIG. 2 shows a specific case of the device illustrated in FIG. 1. It includes all the blocks which are contained in FIG. 1 and which are not set forth in detail once again here. In addition, this device has a telemetry data interface 61 which, in the device shown in FIG. 1, could be included in the block of the other functional units (not specified in greater detail). That telemetry data interface can serve for example for communication with an electromedical implant so that the illustrated device becomes the mediator between an electromedical implant and a home monitoring service center.

Figure 3:
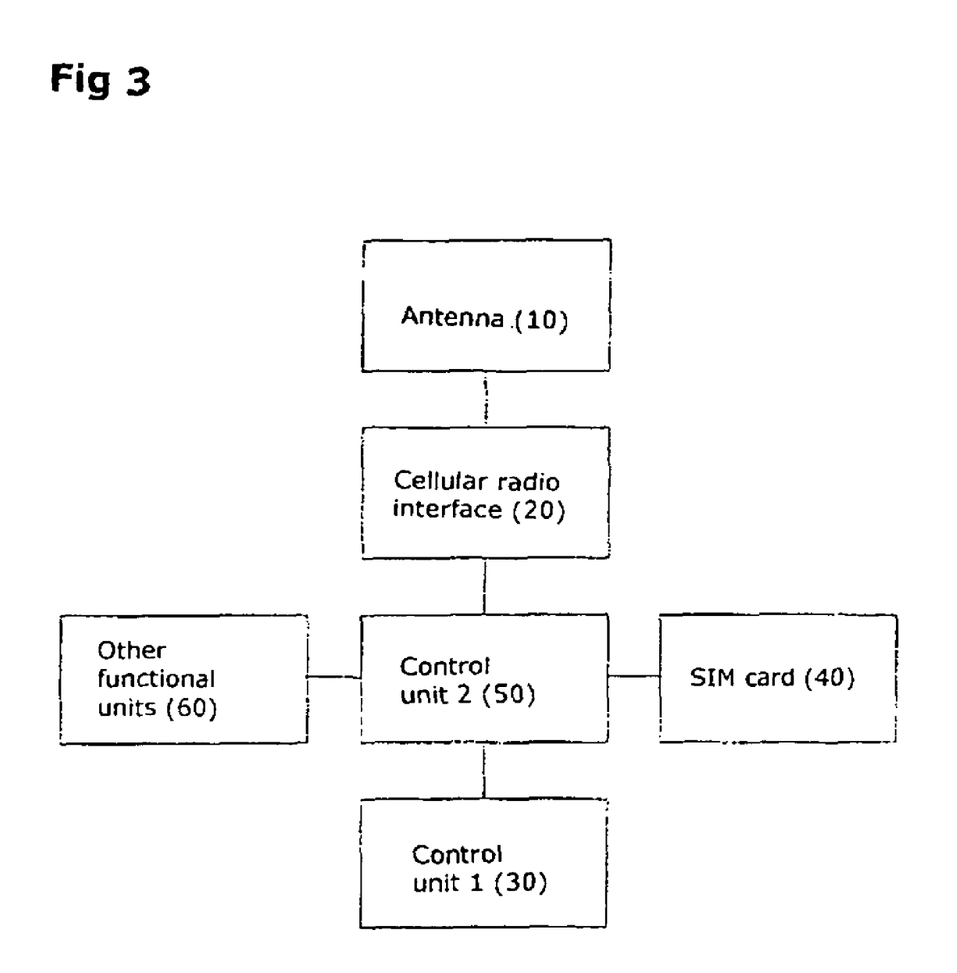
FIG. 3 shows a block diagram of a variant of a device of the kind claimed in claim 1.

FIG. 3 shows an alternative embodiment of the claimed device. The antenna 10 is connected to the cellular radio interface 20, as described hereinbefore. As a departure from the devices shown in the foregoing Figures the cellular radio interface 20 is here connected to the second control unit 50, which in turn is connected to the first control unit 30, the SIM card 40 and the other functional units 60. The other functional units 60 can again include a second telemetry data interface. In this alternative embodiment the second control unit 50 is disposed centrally between the cellular radio interface 20, the SIM card 40, the first control unit 30 and the other functional units 60. In accordance with the current embodiment of the invention it is designed in such a way that it can control and filter the communication between the first control unit 30 and the SIM card 40 and between the cellular radio interface 20 and the first control unit 30 respectively. In that way the second control unit 50 can erase an item of information about a rejection, communicated by that network in respect of which a log-on is attempted, before the first control unit 30 can note that information on the SIM card 40. Alternatively the second control unit 50 could also prevent communication of the evaluated information about the rejection to the SIM card 40 by the first control unit 30, by not passing the information on to the SIM card 40. It is possible to envisage further variants as to the way in which the second control unit 50 nullifies the effect of a rejection by a cellular radio network or limits it in respect of its duration, by control, interruption and alteration of the flow of information between the SIM card 40, the first control unit 50 and the cellular radio interface 20. All those variants are to be embraced by the current embodiment of the subject invention.

Figure 4:
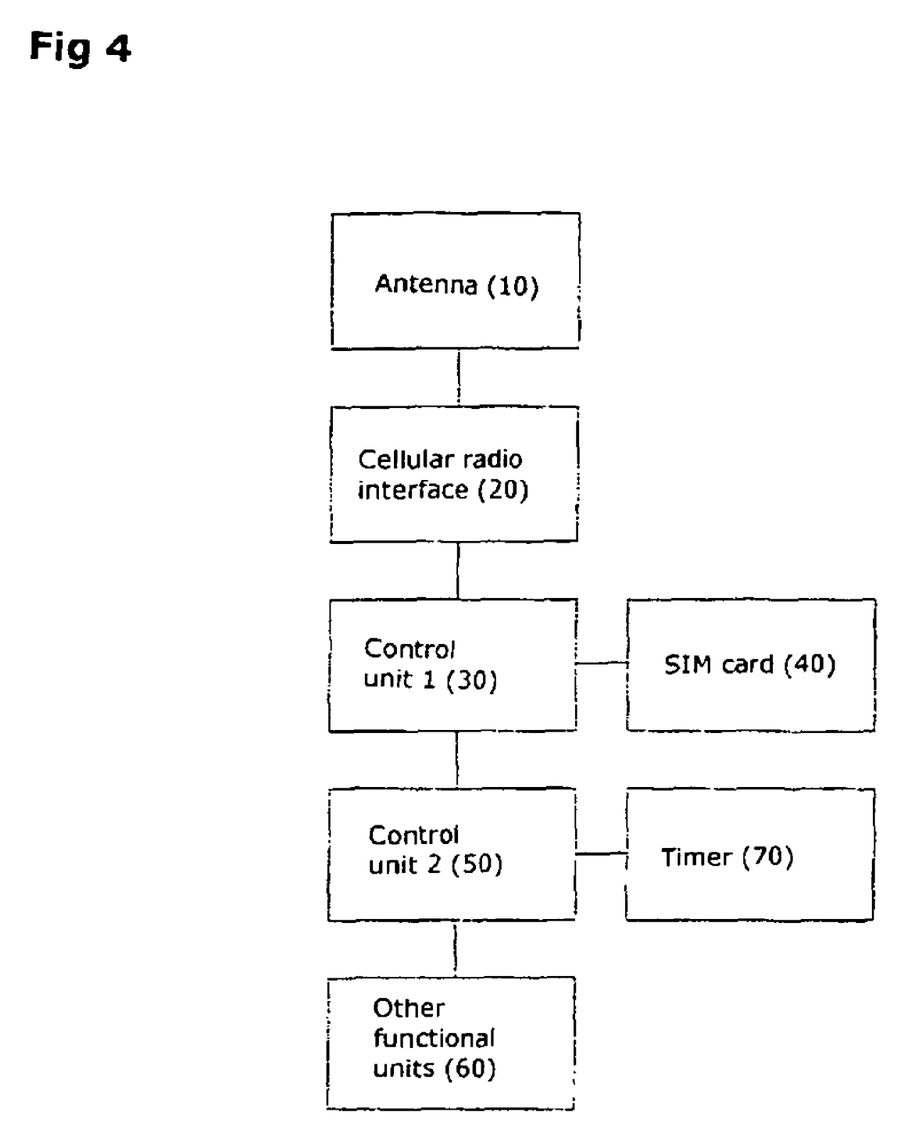
FIG. 4 shows an enlarged block diagram as an embodiment by way of example of a preferred variant as set forth in claims 11, 13 and 14.

FIG. 4 shows a further block diagram of the embodiment of the subject invention. In comparison with the device shown in FIG. 1, the device shown in FIG. 4 additionally has a timer 70 connected to the second control unit 50. The timer 70 measures the configuratable times which are to be allowed to elapse between each step of the method of operation of the embodiment of the subject invention and appropriately signals the elapse of the predetermined times to the second control unit 50.

Figure 5:
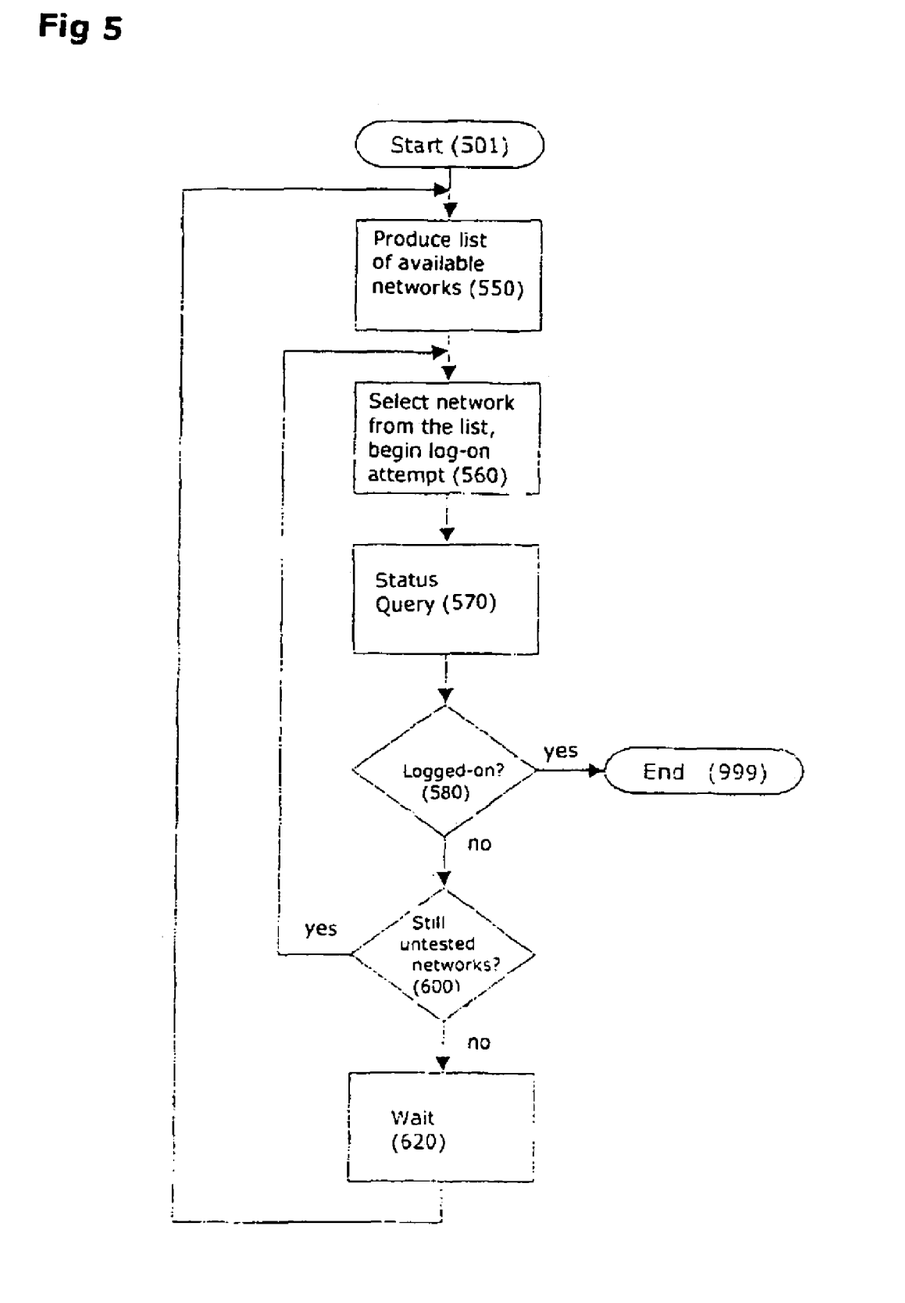
FIG. 5 shows a flow chart of a variant of the method according to the invention.
Figure 6:
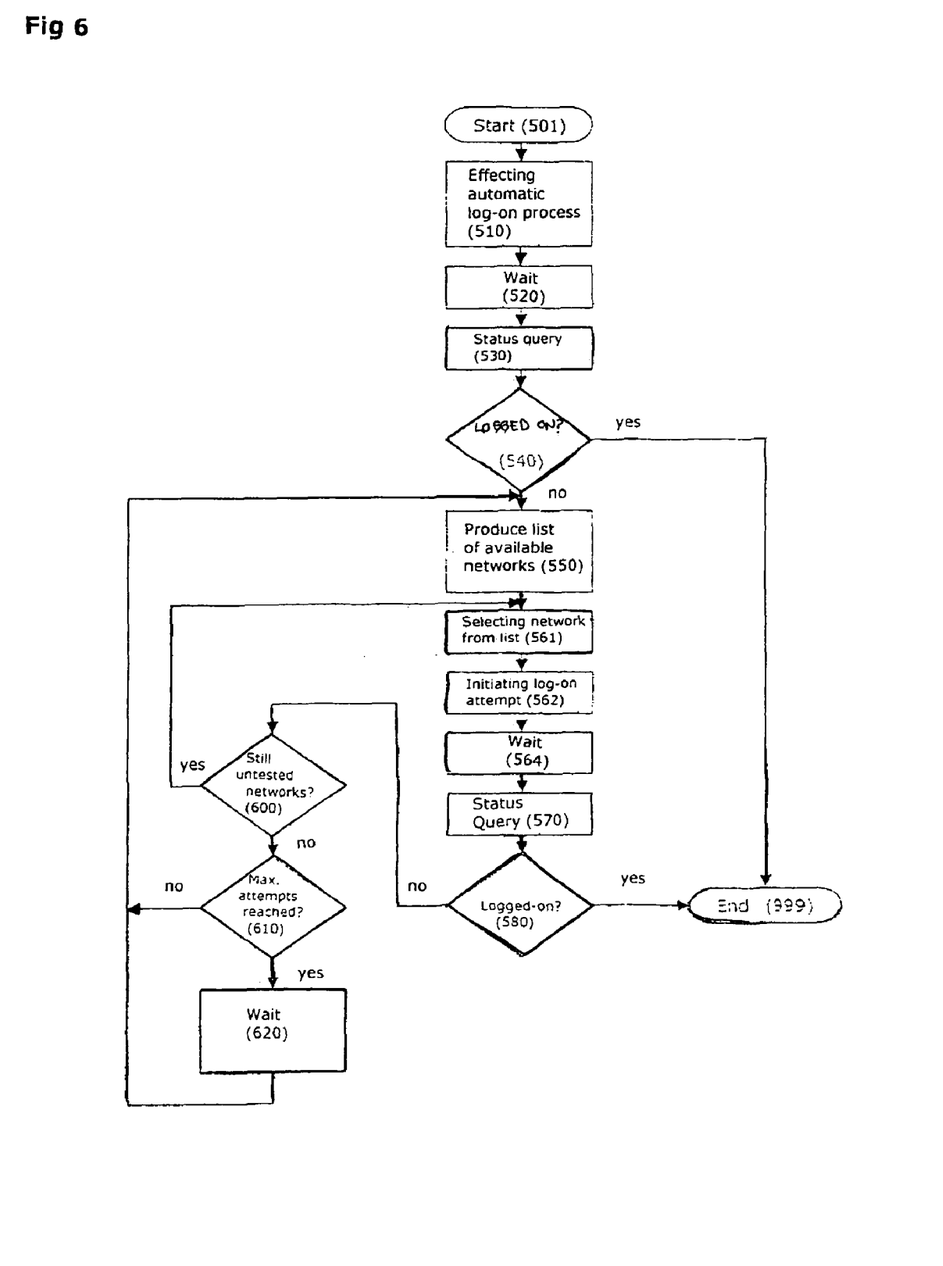
FIG. 6 shows an expanded flow chart of a variant of the method according to the invention.
Figure 7:
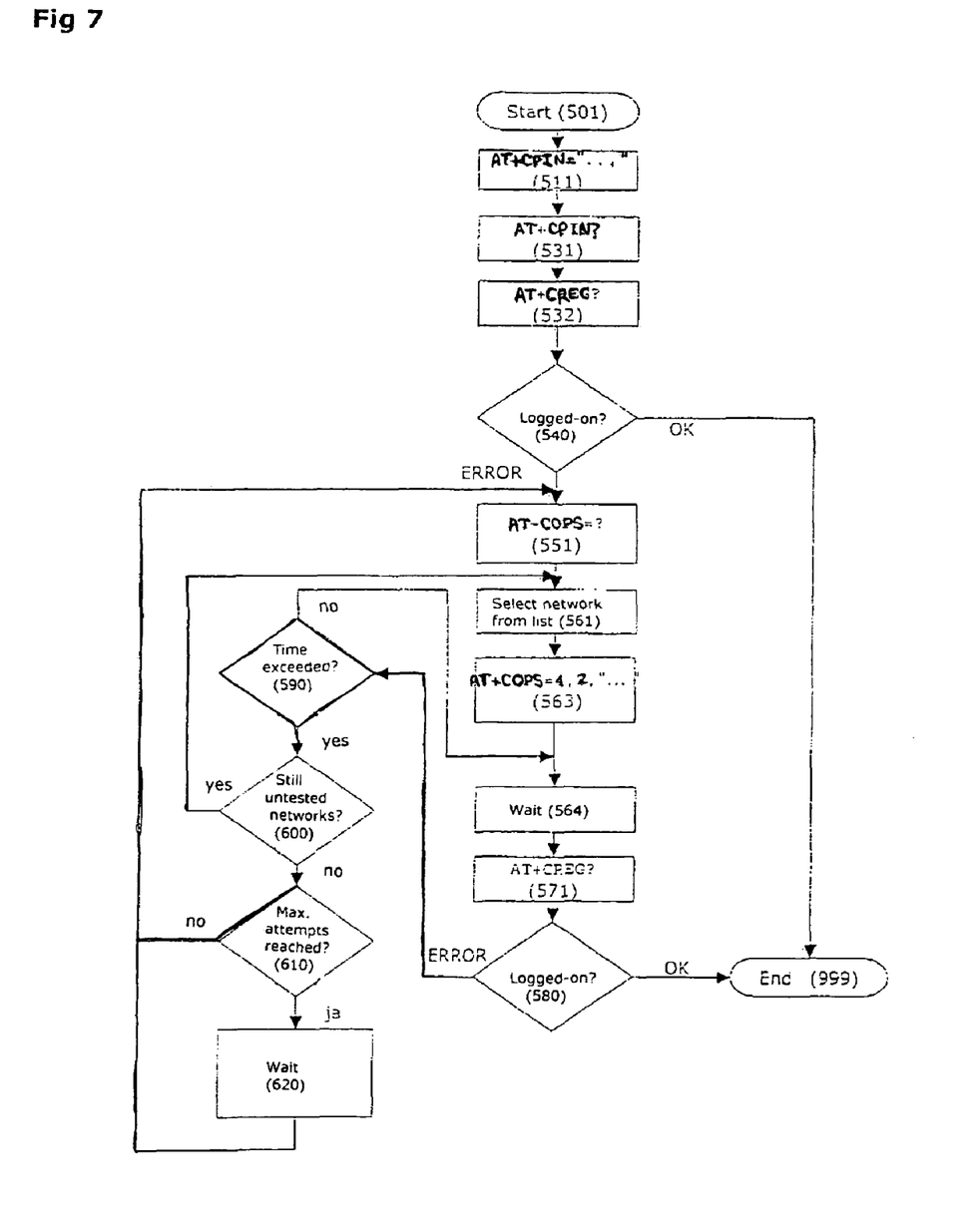
FIG. 7 shows a flow chart of a variant of the claimed method with AT commands for the individual steps.

FIGS. 5 through 7 show flow charts by way of examples of the methods of operation of the embodiment of the subject invention. In all descriptions of flow charts, the numbers in brackets, in accordance with the corresponding method step, specify the numbering in the charts to which the details relate. That occurs wherever the step is not explicitly set out in the set.

FIG. 5 shows a flow chart of an embodiment by way of example of the method of the embodiment of the subject invention. After the start (501), the first step affected is that of producing a list of networks (550) available at the respective location. In the next step a log-on attempt in relation to a selected network from the list is begun (560). Then the status of the cellular radio interface is queried (570) in order to check whether the log-on attempt was successful (580). If the log-on attempt was successful the method is concluded (999). Otherwise, a check is made to ascertain whether the list of the networks available on the spot includes still further networks in relation to which no log-on attempt has yet been made (600), since the list currently being used was produced. If the list has such networks, then the flow chart branches back to the step 560, one of those networks is selected and further proceedings are as before. If the list does not include any further networks, then after an optional waiting pause 620, the flow chart branches back to the step 550 and a fresh list is produced. The method is correspondingly continued until it is concluded with the success case (999).

FIG. 6 shows by way of example an alternate embodiment of the method of the embodiment of the subject invention. Beginning at the start 501, firstly the normal automated log-on process is effected (510). Thereupon the system waits for a given time (520) and then status is queried (530). If the automatic log-on process was successful (540), the method is successfully concluded (999). Otherwise a list of the networks available at the location is produced (550) and a network selected from the list (561). In relation to that network, a log-on attempt is initiated in step 562 and then the system waits for a given predeterminable time (564). A status query is then effected (570) and the result is checked (580). If the device has been successfully logged on with the selected network, the method is then concluded (999). If the contrary is the case, the list being used is checked for further untested networks on the list (600). If such networks are still present on the list, the system branches back to the step 561 and the procedure correspondingly continues. If the list does not include any further untested networks, a check is made to ascertain whether a predetermined maximum number of log-on attempts have been reached (610). That maximum number of log-on attempts can relate to the number of the total log-on attempts made or the number of log-on attempts made per network or the number of processed lists. When the maximum number is reached the log-on attempts are deferred for a predetermined time (620 then back to 550), otherwise the flow chart branches back to the step 550 directly or after a shorter pause than when the maximum number is reached. A variant of this method provides that checking of the maximum number of log-on attempts for each network is also effected individually and that network is excluded from further log-on attempts for a predetermined time when the maximum number of log-on attempts is reached. That is appropriate when the lists vary for example due to changes in location, so that they effect a changing selection of networks. After production of the list of the available networks (550), in an additional step those networks in respect of which the predetermined maximum number of log-on attempts has already been reached are deleted from the list. After the expiry of a time measured individually for each network, the networks are then restored to the produced lists again, if they are available at the location involved.

FIG. 7 shows a flow chart of a similar method to that illustrated in FIG. 6. Here however AT commands are specified as examples in order to explain control of the first control unit 30 (in FIGS. 1 through 4) of an apparatus as set forth herein. At locations where branching is involved in dependence on the result of an AT command, typical responses are "OK" in the success case and "ERROR" in the error case. Starting at 501, the command AT+CPIN="PIN-Code" is outputted in step 511. "PIN-Code" means the so-called PIN code of the SIM card, which in the AT command, is between double quotes (for example: "1234"). That command causes the receiving control unit to communicate the PIN code to the SI card, which compares it to the internally stored copy. That process is not to be confused with communication of the secret user identity information, which is stored on the SIM card to the HLR. The step of checking the PIN code may involve a security mechanism, which was introduced to protect the device from use by persons other than the owner. The PIN code can therefore also usually be selected by the latter. The result of the operation of checking the PIN code which is here not necessarily selected and inputted by the user but which rather is included directly in the control sequence of the control units, consisting of AT commands, is queried in step 531 with the AT command AT+CPIN?. Input of the PIN card normally initiates an automatic log-on process in the case of cellular radio interfaces, which are designed in accordance with the state of the art. The system can wait for the complete implementation thereof by a pause (not shown in the Figure) between the steps 531 and 532. The procedure continues with step 532 by the log-on status being queried with the AT command AT+CREG?. If the device were already successfully logged on in the automatic log-on process, the checking operation in 540 is directly followed by the end of the method (999). Otherwise the receiving control unit in step 551 is instructed by the AT command AT+COPS=? to produce and output a list of the receivable networks. In step 561 a network from the list is selected and a log-on in relation to that network is initiated at 563 by an AT command such as for example AT+COPS=4, 2,"26201". In that respect the third command parameter determines by the five-digit network identification the respective network in relation to which the log-on is to be tried. Step 564 possibly involves waiting for a predetermined time before the log-on status is queried in step 561 with AT+CREG?. Step 564 can be omitted if the status query triggered in step 571 itself already includes a waiting time. If the device has been successfully logged on (580), the method is concluded (999). Otherwise, a check is made to ascertain whether, in the log-on procedure, a predetermined maximum time for log-on has already been exceeded (590). If no time has been exceeded in that respect, the flow chart can branch back to step 564 and the system can again wait. If however the time has been exceeded, then the log-on attempt was unsuccessful and a check is made in step 600 to ascertain whether the used list of available networks still includes entries, which are unchecked at the current time. If there are still such further networks, the flow chart goes back to step 561 and a log-on attempt is affected in relation to one of the unchecked networks. If the list does not contain any further untested networks, a check is made to ascertain whether a predetermined maximum number of log-on attempts have been reached. That maximum number of log-on attempts, as already explained in the description relating to FIG. 6, can relate both to the number of log-on attempts in relation to each individual network within a given period of time and also the number of lists of networks available at the location, which have been processed since the last deferment or the beginning of the log-on procedure. If the maximum number of log-on attempts has been reached, the log-on attempts are deferred by waiting (620), otherwise the flow chart will go back to step 551 after no pause at all or a shorter pause than in 620, and continue to operate with a new list.

We claim:
1. An apparatus having:
at least one telemetry data interface which is adapted to perform a data exchange by way of cellular radio or wireless data networks,
a user identity module containing items of information for operation, including authorization of a user for use of cellular radio or wireless data networks,
a first control unit which controls establishment and implementation of the data exchange on the basis of the items of information stored on the user identity module, adapted to receive a rejection of a user identity by the cellular radio or the wireless data networks when the user identity is rejected during a log-on process,
a second control unit configured to at least temporarily override a rejection of the user identity module by the cellular radio or wireless data networks received by the first unit by bypassing or erasing communicated information about the rejection, and
at least a second telemetry data interface operatively communicated with an associated electromedical implant for use in evaluating data received from the associated electromedical implant and, transmitting the data to a remote monitoring service center,
wherein the apparatus is portable by an associated user,
wherein the telemetry data interfaces are configured to perform the data exchange by way of at least one of a GSM network, UMTS network, CDMA network or WLAN network, wherein at least one of the control units is configured to detect unsuccessful log-on because of rejection by wireless data networks available at a location, and wherein the first control unit is configured to identify a list of locally receivable wireless data networks and wherein the first control unit is adapted to make the list of the locally receivable wireless data networks accessible to the second control unit.

2. The apparatus as set forth in claim 1, wherein the second control unit is configured to select a further network from the list after a failed log-on in relation to a wireless data network; and, wherein the second control unit is configured to cause the first control unit to implement a log-on attempt to the wireless data network if the network had already rejected a log-on in a preceding attempt.

3. The apparatus as set forth in claim 2, wherein the second control unit is configured to produce at least a second list of the locally receivable wireless data networks by the first control unit after an unsuccessful log-on attempt to all networks on the first list of the locally receivable wireless data networks.

4. The apparatus as set forth in claim 3, wherein the second control unit is operatively connected to a timer, the second control unit being adapted such that after a failed log-on to cause the elapse of a predetermined period of time measured by the timer before the second control unit initiates a further log-on attempt in relation to the same network.

5. The apparatus as set forth in claim 4, wherein the first and second control units are adapted to execute AT commands.

6. The apparatus as set forth in claim 5, wherein the second control unit defers repeated unsuccessful log-on attempts in relation to the locally available wireless data networks for a given time measured by the timer.

7. The apparatus as set forth in claim 6, wherein the second control unit is configured to predetermine and alter operating parameters between the maximum number of log-on attempts and the maximum time involved for a log-on attempt before the log-on attempt is broken off as being unsuccessful.

8. The apparatus as set forth in claim 7 wherein the second control unit is operatively connected to the telemetry data interfaces so that the choice of the parameters can be triggered from the remote monitoring service center by way of the telemetry data interfaces.

9. A method of operating a wireless communication apparatus, comprising the steps of:

providing an apparatus adapted to perform a data exchange by way of an associated wireless data network, a user identity module containing items of information about an authorized operation of the associated wireless data network, a first control unit which controls implementation of the wireless data exchange on the basis of the items of information stored on the user identity module adapted to receive a rejection of a user identity by cellular radio or wireless data networks when the user identity is rejected during a log-on process, a second control unit configured to at least temporarily override the rejection of the user identity by the cellular radio or wireless data networks received by the first unit by bypassing or erasing communicated information about the rejection, and first and second telemetry data interfaces wherein the first telemetry data interface is adapted to perform a data exchange by way of cellular radio or wireless data networks and the second telemetry data interface is in operative communication with an associated electromedical implant for use in evaluating data received from the associated electromedical implant and, transmitting the data to a remote monitoring service center;

rejecting a log-on attempt of the apparatus by the associated wireless data network;

detecting the first unsuccessful log-on because of the rejection by the associated wireless data network;

overriding the rejection of the log-on attempt by bypassing communicated messages from the associated wireless data network about the rejection; and producing a list of one or more locally receivable associated wireless data networks onto which the apparatus can attempt to log-on.

10. The method as set forth in claim 9, further comprising the steps of:

prioritizing the sequence of the list of the locally receivable associated wireless data networks so that the associated wireless data networks with a higher signal reception strength are preferred during log-on attempts by the apparatus.

11. The method as set forth in claim 10, wherein after the step of rejecting a log-on attempt by the associated wireless data networks, the steps further comprising:

selecting the next prioritized associated wireless data network from the list after a failed log-on in relation to a preceding associated wireless data network is completed, and, attempting to log-on to an associated wireless data network even if that associated wireless data network had already been rejected in a preceding log-on attempt.

12. The method as set forth in claim 11, wherein the list of one or more locally receivable associated wireless data networks is a first list of one or more locally receivable associated wireless data networks; and, further comprising the steps of:

producing at least a second list of locally receivable associated wireless data networks after unsuccessful log-on attempts to all of the associated wireless data networks of the first list is completed.

13. The method as set forth in claim 12, further comprising the steps of:

deeming a log-on attempt failed after a predetermined time has elapsed in relation to not receiving a positive return message from an associated wireless data network.

14. The method as set forth in claim 13, further comprising the steps of:

causing a predetermined time to elapse after a failed log-on attempt before a second log-on attempt is initiated in relation to the same network.

15. The method as set forth in claim 14, further comprising the steps of:

deferring subsequent log-on attempts in relation to the same or to other associated wireless data networks for a predetermined period of time after a predetermined number of failed log-on attempts has occurred.

16. The method as set forth in claim 15, further comprising the steps of:

establishing whether a log-on attempt was successful in relation to one of the associated wireless data networks thereby concluding additional attempts at logging-on to another associated wireless data networks.

* * * * *